United States Patent
Aubanel et al.

(10) Patent No.: US 7,319,516 B2
(45) Date of Patent: Jan. 15, 2008

(54) MEASUREMENT INSTRUMENT FOR INSPECTING PAINTED BODYWORK PARTS, THE INSTRUMENT BEING PROVIDED WITH AN ANTI-DAMAGE DEVICE

(75) Inventors: Laurent Aubanel, Villette sur Ain (FR); Patrick Magnier, Parmilieu (FR); Laurent Dam, Priay (FR)

(73) Assignee: Compagnie Plastic Omnium, Lyons (FR)

( * ) Notice: Subject to any disclaimer, the term of this patent is extended or adjusted under 35 U.S.C. 154(b) by 179 days.

(21) Appl. No.: 11/184,255

(22) Filed: Jul. 18, 2005

(65) Prior Publication Data
US 2006/0061767 A1 Mar. 23, 2006

(30) Foreign Application Priority Data
Jul. 19, 2004 (FR) .................................. 04 07984

(51) Int. Cl.
*G01N 21/00* (2006.01)
(52) U.S. Cl. .................................. 356/237.1; 356/237.2
(58) Field of Classification Search .................... None
See application file for complete search history.

(56) References Cited
U.S. PATENT DOCUMENTS 4,715,709 A 12/1987 Sekine et al.
4,853,879 A 8/1989 Matzoll, Jr. et al.
5,237,404 A 8/1993 Tanaka et al.
5,773,840 A 6/1998 Pryor et al.
2002/0120359 A1* 8/2002 Xi et al. ...................... 700/184

FOREIGN PATENT DOCUMENTS

| EP | 1 076 221 A2 | 2/2001 |
| EP | 1 429 114 A2 | 6/2004 |
| WO | WO 87/00629 | 1/1987 |

* cited by examiner

*Primary Examiner*—Michael P. Stafira
(74) *Attorney, Agent, or Firm*—Robert L. Epstein; Epstein Drangel Bazerman & James, LLP

(57) ABSTRACT

The invention relates to an optical measurement instrument for inspecting the quality of paintwork at the outlet from a line for painting motor vehicle bodywork parts, the instrument including a viewing frame through which the instrument takes optical measurements. In front of the viewing frame, the instrument includes a contact sensor suitable for indicating any contact between the instrument and an obstacle.

3 Claims, 1 Drawing Sheet

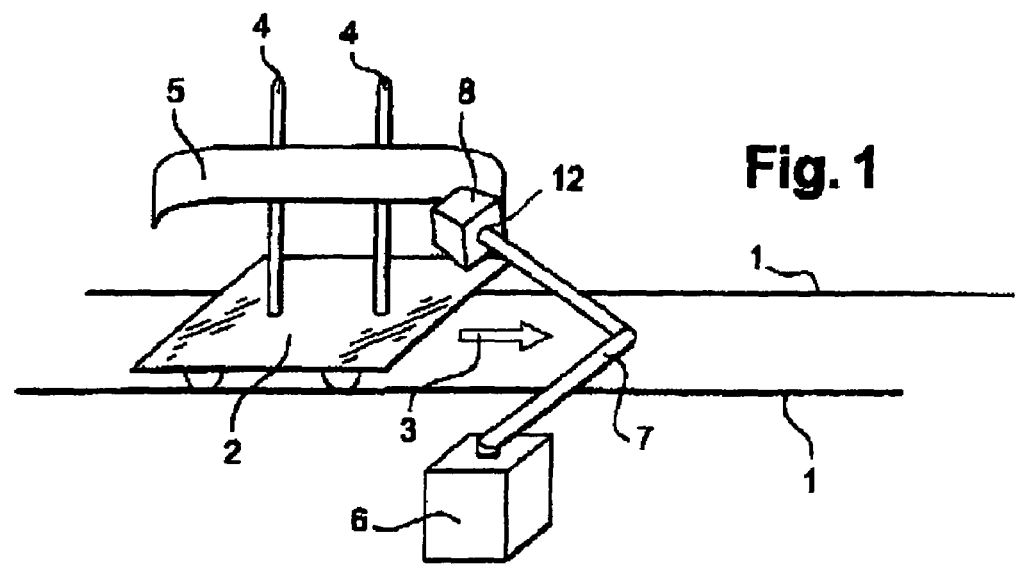
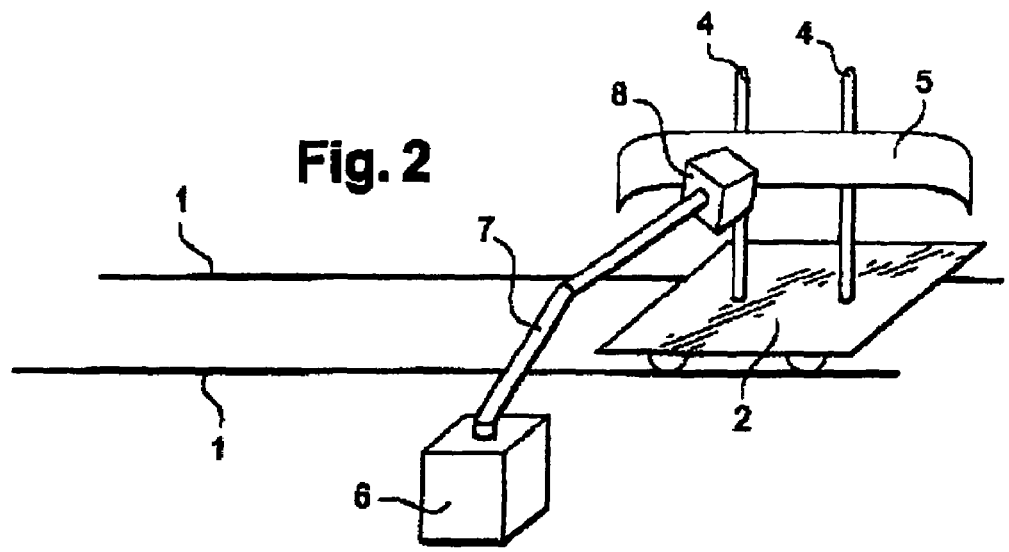
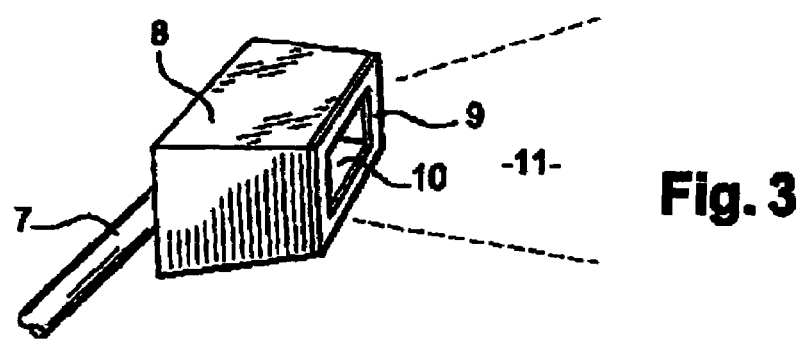

MEASUREMENT INSTRUMENT FOR INSPECTING PAINTED BODYWORK PARTS, THE INSTRUMENT BEING PROVIDED WITH AN ANTI-DAMAGE DEVICE

The present invention relates to a measurement instrument for inspecting painted bodywork parts, the instrument being provided with an anti-damage device.

BACKGROUND OF THE INVENTION

Optical measurement devices are known that are used at the outlets from lines for painting bodywork parts in order to verify the appearance of the parts, e.g. their hue, their pinpoint blistering, the leveling of their painting, or their brilliance.

In general, the optical measurement instruments used at the outlet from painting lines are stationary and they see the bodywork parts for inspection pass through their field of view, with the parts usually standing still for a period of sufficient duration to allow the measurement to be performed.

Such instruments are located at a certain distance from the parts to be inspected, which keeps them safe from any risk of being damaged by an untimely impact against a moving part.

Nevertheless, in the most recent painting inspection stations, the measurement instrument is no longer stationary, but is carried by a robot arm that presents it in the proximity of the part to be inspected at different locations thereof in order to take a plurality of measurements at predetermined angles of view.

Under such circumstances, the instrument comes very close to the surface of the part, thereby considerably increasing the risk of collision between the instrument and the part.

The consequences of such a collision can be very severe, particularly given the price of instruments of this kind.

OBJECTS AND SUMMARY OF THE INVENTION

The invention seeks to propose a solution for providing the measurement instrument with effective protection regardless of the circumstances under which measurement is performed, and in particular when said instrument is moved by a robot.

The present invention provides an optical measurement instrument for inspecting the quality of paintwork at the outlet from a line for painting motor vehicle bodywork parts, the instrument including a viewing frame through which the instrument takes optical measurements, the instrument including, in front of the viewing frame, a contact sensor suitable for indicating any contact between the instrument and an obstacle.

Because of its contact sensor, the instrument of the invention can avoid being subjected to excessive forces from any obstacle with which it might come into collision, since in the event of the contact sensor providing a signal, a response can be triggered immediately, before the instrument is damaged.

By way of example, such a response can consist in causing the robot to pull back the instrument, or in causing the conveyor of the basic line to stop moving the part.

Various known devices can be used for constituting such a sensor. In particular, in a particular embodiment of the invention, it is possible to use a resistive sensor such as the sensor in the from of a strip that is sold by the French supplier SAVERKA under the reference 141BPH.

According to optional characteristics of the invention that can be used singly or in combination:
- the measurement instrument is suitable for taking measurements at a point on at least two different angles, and preferably at three to five angles;
- the measurement instrument is suitable for providing data concerning the hue, the leveling, the pinpoint blistering, and/or the brilliance of the painting;
- the instrument includes fastener means for mounting it on a robot; and
- the instrument is designed to occupy an inspection station at the outlet from a line for painting bodywork parts, separate from a line for painting "bodies-in-white".

BRIEF DESCRIPTION OF THE DRAWINGS

In order to make the invention better understood, there follows a description of an embodiment given by way of an example that does not limit the scope of the invention, and described with reference to the accompanying drawing, in which:

FIG. 1 is a perspective view of an inspection station at the outlet from a painting line;

FIG. 2 is a view analogous to FIG. 1, showing the same inspection station after the conveyor has advanced; and FIG. 3 is a perspective view of a measurement instrument in an embodiment of the invention.

MORE DETAILED DESCRIPTION

As can be seen in FIGS. 1 and 2, the inspection station is situated on the path of a conveyor having rails 1 that are shown diagrammatically. A carriage 2 runs along the rail 1 and is moved, by means that are not shown, in the direction indicated by the arrow 3.

The carriage 2 has two masts 4 carrying a bumper 5 of plastics material that has just been painted in the painting line.

The inspection station comprises a robot 6 having an arm 7 causing an optical measurement instrument 8 by means of fastener means 12.

The arm 7 presents the instrument 8 in a position that is suitable for taking an inspection measurement. The carriage 2 may be caused to stop temporarily during measurement.

In the present description, details concerning the taking of a measurement and the technology to be used for this purpose are not provided. The person skilled in the art can refer to the available technical documentation, for example that associated with the "CARFLASH" device from the American supplier X-RITE.

In order to enable the measurement instrument to take measurements at different locations of the bumper 5, the carriage 2 can advance a little along the rails 1 so as to stand still in a new measurement position as shown in FIG. 2, in which the arm 7 presents the measurement instrument 8 in a different manner relative to the bumper 5.

The movements of the arm 7 are programmed in a control device (not shown) of the robot as a function of the inspected path of the bumper 5, which path is normally in translation parallel to the rail 1, and also as a function of the expected position for the bumper 5 on the two masts 4.

Nevertheless, it can happen that the real position of the bumper is not exactly the expected position, for example as a result of an incident that has occurred during painting.

If such circumstances should arise, or if any other unexpected circumstance should arise that change the path of the bumper 5, the measurement instrument 8 moved by the robot along a predetermined path runs the risk of coming into collision with the bumper 5.

In order to avoid the consequences of such a collision, and as can be seen in FIG. 3, the measurement instrument 8 includes a contact sensor 9 which is disposed at the periphery of its viewing opening 10 or viewing frame that defines its field of view 11.

The contact sensor 9 can detect any obstacle coming into contact with the periphery of the opening 10 and can send a detection signal to a response device (not shown), which can act, for example, to stop the conveyor so that even in the event of contact occurring between the measurement instrument and the bumper 5, no force is applied to the measurement instrument.

The measurement instrument as protected in this way is protected from any risk of damage.

Naturally, the signal coming from the contact sensor 9 may be set to any other response device, and in particular to the control device of the robot.

Naturally, the invention described above does not present any limiting character and could receive any desirable modification without thereby going beyond the ambit of the invention.

What is claimed is:

1. An optical measurement instrument for inspecting the quality of paintwork at the outlet from a line for painting motor vehicle bodywork parts, the instrument including a viewing frame through which the instrument takes optical measurements, the instrument including, in front of the viewing frame and disposed onto this viewing frame, a contact sensor suitable for indicating contact between the instrument and an obstacle.

2. An instrument according to claim 1, including fastener means for mounting it on a robot.

3. An instrument according to claim 1, for occupying an inspection station at the outlet from a line for painting bodywork parts, and separate from a line for painting bodies-in-white.

* * * * *